(12) United States Patent
Canaud (10) Patent No.: US 12,427,141 B2
(45) Date of Patent: *Sep. 30, 2025

(54) BYL719 (ALPELISIB) FOR USE IN THE TREATMENT OF PIK3CA-RELATED OVERGROWTH SPECTRUM (PROS-CLOVES SYNDROME)

(71) Applicants: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ PARIS CITÉ, Paris (FR); ASSISTANCE PUBLIQUE—HÔPITAUX DE PARIS (APHP), Paris (FR)

(72) Inventor: Guillaume Canaud, Paris (FR)

(73) Assignees: INSERM (INSTITUT NATIONAL DE LA SANTÉ ET DE LA RECHERCHE MÉDICALE), Paris (FR); CENTRE NATIONAL DE LA RECHERCHE SCIENTIFIQUE (CNRS), Paris (FR); UNIVERSITÉ PARIS CITÉ, Paris (FR); ASSISTANCE PUBLIQUE—HÔPITAUX DE PARIS (APHP), Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/721,067

(22) Filed: Apr. 14, 2022

(65) Prior Publication Data
US 2022/0323428 A1 Oct. 13, 2022

Related U.S. Application Data

(63) Continuation of application No. 15/998,950, filed as application No. PCT/EP2017/053587 on Feb. 17, 2017, now Pat. No. 11,433,059.

(30) Foreign Application Priority Data

Feb. 19, 2016 (EP) .................................. 16305193

(51) Int. Cl.
A61K 31/4439 (2006.01)
A61P 43/00 (2006.01)
(52) U.S. Cl.
CPC .......... *A61K 31/4439* (2013.01); *A61P 43/00* (2018.01)
(58) Field of Classification Search
CPC ............................ A61P 43/00; A61K 31/4439
See application file for complete search history.

(56) References Cited

U.S. PATENT DOCUMENTS 11,433,059 B2    9/2022   Canaud

FOREIGN PATENT DOCUMENTS

WO    WO 2016187157 A1    11/2016

OTHER PUBLICATIONS

Uller et al (Seminars in Pediatric Surgery, 2014; 23(4):208-215) (Year: 2014).*
Luks et al (J Pediatr 2015; 166(4):1048-54, see p. 1050, left, last paragraph) (Year: 2015).*
Limaye et al., "Somatic Activating PIK3CA Mutations Cause Venous Malformation", *The American Journal of Human Genetics*, 97(6):914-921, Dec. 2015, doi:10.1016/J.AJHG.2015.11.011, ISSN 0002-9297.
Kurek et al., "Somatic Mosaic Activating Mutations in PIK3CA Cause CLOVES Syndrome", *The American Journal of Human Genetics*, 90:1108-1115, 2012.
Vahidnezhad et al., "Klippel-Trenaunay syndrome belongs to the PIK3CA-related overgrowth spectrum (PROS)", *Experimental Dermatology*, 25(1):17-19, first published online Aug. 13, 2015.
Written Opinion of the International Searching Authority for International Application No. PCT/EP2017/053587, dated Aug. 24, 2017, 5 pages.
Mirzaa et al., "PIK3CA-Related Overgrowth Spectrum", GeneReviews, pp. 1-30 (Aug. 2013), https://www.ncbi.nlm..nih.gov/books/NBK153722/pdf/Bookshelf NBK153722.pdf.
Crunkhorn, "PI3K inhibitor reverses overgrowth syndrome", Nature Reviews Drug Discovery 17(8):545, doi:10.1038/nrd.2018.120 (2018).
Delestre et al., "Alpelisib administration reduced lymphatic malformations in a mouse model and in patients", *Science Translational Medicine* 13(614):eabg0809 (2021).
Delestre et al., "Supplementary Materials for Alpelisib administration reduced lymphatic malformations in a mouse model and in patients", *Science Translational Medicine* 13(614):eabg0809 (2021).
Ladraa et al., "PIK3CA gain-of-function mutation in adipose tissue induces metabolic reprogramming with Warburg-like effect and severe endocrine disruption", *Science Advances* 8:eade7823 (2022).
Morin et al., "Treatment of two infants with PIK3CA-related overgrowth spectrum by alpelisib", *Journal of Experimental Medicine* 219(3):e20212148 (2022).

(Continued)

*Primary Examiner* — Rayna Rodriguez
(74) *Attorney, Agent, or Firm* — Lathrop GPM LLP; Brian C. Trinque; Nicole Sassu (57) ABSTRACT

The present invention relates to a method of treating PIK3CA-Related Overgrowth Spectrum (PROS) more particularly, Congenital, Lipomatous, Overgrowth, Vascular Malformations, Epidermal Nevi and Spinal/Skeletal Anomalies and/or Scoliosis (CLOVES) syndrome. To date, there are no specific treatments for patients and no animal models of PROS to better understand the physiopathology of the disorder. Inventors developed a genetic mouse model of PROS that recapitulates the human disease and demonstrated the efficacy of BYL719. Based on these results they treated two patients, one adult and one child, with severe CLOVES syndrome using BYL719. The drug had a robust efficiency on disease in the two patients inducing quick recovery of all affected organs. Thus, the invention relates to a method of treating PROS in a subject in need thereof comprising the step of administrating the subject with a therapeutically effective amount of BYL719.

14 Claims, 4 Drawing Sheets

(56) References Cited

OTHER PUBLICATIONS

Semple et al., "Cancer drug tackles overgrowth syndrome", *Nature* 558(7711):523-525 (2018).
Venot et al., "Targeted therapy in patients with PIK3CA-related overgrowth syndrome", *Nature* 558(7711):540-546 (2018).
FDA Accelerated Approval; https://www.fda.gov/patients/fast-track-breakthrough-therapy-accelerated-approval-priority-review/accedlrated-approval.
"FDA approves alpelisib for PIK3CA-related overgrowth spectrum", United States Food and Drug Administration (FDA) (2022).
"FDA Approves Novartis Vijoice® for Select Patients with PIK3CA-Related Overgrowth Spectrum", American Pharmaceutical Review Press Release, Apr. 6, 2022, https://www.americanpharmaceuticalreview.com/1315-News/584880-FDA-Approves-Novartis-Vijoice-for-Select-Patients-with-PIK3CA-Related-Overgrowth-Spectrum/.
Novartis Annual Report 2023.
Adams et al., "Efficacy and Safety of Sirolimus in the Treatment of Complicated Vascular Anomalies", *Pediatrics* 137(2):e20153257 (2016).
Alomari, "Characterization of a distinct syndrome that associates complex truncal overgrowth, vascular, and acral anomalies: a descriptive study of 18 cases of CLOVES syndrome", *Clinical Dysmorphology* 18(1): -7 (2009).
Canaud et al., "A review of mechanisms of disease across PIK3CA-related disorders with vascular manifestations", *Orphanet Journal of Rare Diseases* 16:306 (2021).
Di Blasio et al., "PI3K/mTOR inhibition promotes the regression of experimental vascular malformations driven by PIK3CA-activating mutations", *Cell Death & Disease* 9(2):45 (2018).
Dompmartin et al., "Venous Malformation: update on etiopathogenesis, diagnosis & management", *Phlebology* 25(5):224-235 (2010).
Forde et al., "Clinical experience with the AKT1 inhibitor miransertib in two children with PIK3CA-related overgrowth syndrome", *Orphanet Journal of Rare Diseases* 16(1):109 (2021).
Friedberg, "Gigantic Growth of the Right Leg", Archives for Pathological Anatomy and Physiology vol. XL, Hn. 3u. 4 (1867).
Keppler-Noureuil et al., "PIK3CA-Related Overgrowth Spectrum (PROS): Diagnostic and Testing Eligibility Criteria, Differential Diagnosis, and Evaluation", *American Journal of Medical Genetics* 0(2):287-295 (2015).
Lopez Gutierrez et al., "Alpelisib Treatment for Genital Vascular Malformation in a Patient with Congenital Lipomatous Overgrowth, Vascular Malformations, Epidermal Nevi, and Spinal/Skeletal Anomalies and/or Scoliosis (CLOVES) Syndrome", *Journal of Pediatric and Adolescent Gynecology* 32(6):648-650 (2019).
Luu et al., "Safety and efficacy of low-dose PI3K inhibitor taselisib in adult patients with CLOVES and Klippel-Trenaunay syndrome (KTS): the TOTEM trial, a phase 1/2 multicenter, open-label, single-arm study", *Genetics in Medicine* 23(12):2433-2442 (2021).
Pagliazzi et al., "PIK3CA-Related Overgrowth Spectrum From Diagnosis to Targeted Therapy: A Case of CLOVES Syndrome Treated With Alpelisib", *Frontiers in Pediatrics* 9(9):732836 (2021).
Parker et al., "Safety and efficacy of low-dose sirolimus in the PIK3CA-related overgrowth spectrum", *Genetics in Medicine* 21(5):1189-1198 (2019).
Reis III et al., "Pulmonary thromboembolic events in patients with congenital lipomatous overgrowth, vascular malformations, epidermal nevi, and spina;/skeletal abnormalities and Klippel-Trenaunay syndrome", *Journal of Vascular Surgery: Venous and Lymphatic Disorders* 6(4):511-516 (2018).
Sapp et al., "Newly delineated syndrome of congenital/lipomatous overgrowth, vascular malformations, and epidermal nevi (CLOVE) syndrome) in seven patients", *American Journal of Medical Genetics, Part A* 143A(24):2944-2958 (2007).
Seront et al., "Preliminary results of the European multicentric phase III trial regarding sirolimus in slow-flow vascular malformations", *JCI Insight* 8(21):e173095 (2023).
Zerbib et al., "Targeted therapy for capillary-venous malformations", *Signal Transduction and Targeted Therapy* 9:146 (2024). PMCID: PMC11180659.

\* cited by examiner

BYL719 (ALPELISIB) FOR USE IN THE TREATMENT OF PIK3CA-RELATED OVERGROWTH SPECTRUM (PROS-CLOVES SYNDROME)

RELATED APPLICATIONS

This application is a continuation of U.S. patent application Ser. No. 15/998,950, filed Aug. 17, 2018, which is a 35 U.S.C. § 371 filing of International Patent Application No. PCT/EP2017/053587, filed Feb. 17, 2017, which claims priority to European Patent Application No. 16305193.1, filed Feb. 19, 2016, the entire disclosures of which are hereby incorporated herein by reference.

FIELD OF THE INVENTION

The invention relates to methods for the treatment of PIK3CA-related overgrowth spectrum (PROS), such as congenital lipomatous overgrowth, vascular malformations and epidermal nevi (CLOVES).

BACKGROUND OF THE INVENTION

The term "PROS" for PIK3CA-Related Overgrowth Spectrum" was agreed upon to encompass both the known and emerging clinical entities associated with somatic PIK3CA mutations including, macrodactyly, FAO, HHML, CLOVES, and related megalencephaly conditions (Keppler-Noreuil et al 2014). A workshop was convened at the National Institutes of Health (NIH) to discuss and develop a consensus document regarding diagnosis and treatment of patients with PIK3CA-associated somatic overgrowth disorders.

CLOVES, stands for Congenital, Lipomatous, Overgrowth, Vascular Malformations, Epidermal Nevi and Spinal/Skeletal Anomalies and/or Scoliosis. This syndrome is considered as a rare disorder and characterised by progressive, complex, and mixed truncal vascular malformations, dysregulated adipose tissue, varying degrees of scoliosis, and enlarged bony structures without progressive bony overgrowth (Sapp et al 2007; Alomari et al 2009). This syndrome is different from cancer. In fact, in CLOVES syndrome, tumours are benign, the tissues are just overgrowth and the subject is deformed. CLOVES syndrome is rare and evident at birth. It affects males and females equally regardless of their race or ethnicity. Many of the patients with this syndrome are misdiagnosed.

CLOVES syndrome is caused by a somatic mosaic mutation in PIK3CA gene. PIK3CA encodes the 110-kD catalytic alpha subunit of PI3K, which in response to tyrosine kinase receptor ligand binding is activated and converts phosphatidylinositol (3,4)-bisphosphate (PIP2) to phosphatidylinositol (3,4,5)-triphosphate (PIP3). Activating mutations in PIK3CA have been described in several types of cancers but never in CLOVES syndrome. In 2012, Kurek et al has identified the activating mutations in PIK3CA by sequencing DNA or RNA. But, today, there is no cure for CLOVES Syndrome.

Limaye et al 2015 discloses that somatic mutations in PIK3CA are involved in cancers, overgrowth syndromes, and lymphatic malformation (LM). More particularly, the authors showed that cultured cell lines derived from healthy donors (not affected by PROS), called human umbilical venous endothelial cells (HUVEC) then retrovirally transfected with mutant PIK3CA have an activation of the AKT/mTORC pathway. The drug BYL719 abolished, as expected, PIK3CA-variant induced AKT phosphorylation in this artificial model, indicating that these proteins participate in the same signalling pathway. But, this in vitro model does not recapitulate any symptom or disease phenotype related to PROS patients, more particularly does not show any evidence that this drug could be used to treat patients suffering from PROS. Thus, there is a need to understand the use of BYL719 in patients with PROS, more particularly with CLOVES syndrome or Klippel-Trenaunay syndrome.

SUMMARY OF THE INVENTION

The present invention relates to a method of treating PROS in a subject in need thereof comprising a step of administrating the subject with a therapeutically effective amount of BYL719. In particular, the present invention is defined by the claims.

DETAILED DESCRIPTION OF THE INVENTION

BYL719 synthesized by Novartis is in clinical trial at phase II/III for advanced solid tumours. Inventors developed the first genetic mouse model of PROS that recapitulates the human disease and demonstrated the efficacy of BYL719, a pharmacological inhibitor of PIK3CA, in preventing and improving all organs dysfunction in the PROS mouse. Based on these results they treated two patients, one adult and one child, with severe CLOVES syndrome using BYL719. The drug had a robust efficiency on disease in the two patients inducing quick recovery of all affected organs. Previously intractable vascular tumors shrunk, congestive heart failure fully recovered, hemi hypertrophy reduced, and scoliosis was attenuated. The drug was not associated with any significant side effects. In conclusion, this study provides the first direct evidence supporting PIK3CA inhibition as a promising therapeutic in PROS patients.

Accordingly, the present invention relates to a method of treating PROS in a subject in need thereof comprising a step of administrating the subject with a therapeutically effective amount of BYL719. More particularly, the invention relates to a method of treating CLOVES syndrome in a subject in need thereof comprising the step of administrating the subject with a therapeutically effective amount of BYL719.

As used herein, the terms "treating" or "treatment" refer to both prophylactic or preventive treatment as well as curative or disease modifying treatment, including treatment of subject at risk of contracting the disease or suspected to have contracted the disease as well as subject who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a subject during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a subject during treatment of an illness, e.g., to keep the subject in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., pain, disease manifestation, etc.]).

As used herein the term "PROS" refers to PIK3CA-Related Overgrowth Spectrum. It is a group of disorders such as fibroadipose overgrowth (FAO), megalencephaly-capillary malformation (MCAP) syndrome, congenital lipomatous asymmetric overgrowth of the trunk, lymphatic, capillary, venous, and combined-type vascular malformations, epidermal nevi, skeletal and spinal anomalies (CLOVES) syndrome and Hemihyperplasia Multiple Lipomatosis (HHML) and Klippel-Trenaunay syndrome.

As used herein, the term "fibroadipose overgrowth (FAO)" refers to a syndrome, which is characterized by the major findings of segmental progressive overgrowth of subcutaneous, muscular, and visceral fibroadipose tissue with skeletal overgrowth (Lindhurst et al 2012).

As used herein, the term "megalencephaly-capillary malformation (MCAP) syndrome" refers to a syndrome which is characterized by the major findings of (1) megalencephaly (MEG) or hemimegalencephaly (HMEG) associated with neurologic findings of hypotonia, seizures, and mild to severe intellectual disability; and (2) cutaneous capillary malformations with focal or generalized somatic overgrowth (Mirzaa et al 2013).

In a particular embodiment, the PROS disorder is CLOVES. As used herein, the term "CLOVES" refers to Congenital, Lipomatous, Overgrowth, Vascular Malformations, Epidermal Nevi and Spinal/Skeletal Anomalies and/or Scoliosis. This syndrome is characterised by lipomatous tissues showing complex congenital overgrowth (typically appearing as a truncal lipomatous mass) and a combination of vascular and lymphatic malformations.

As used herein, the term "Hemihyperplasia Multiple Lipomatosis (HHML)" refers to a condition characterized by asymmetric nonprogressive overgrowth, multiple lipomas, and superficial vascular malformations (BG et al 2013).

In a particular embodiment, the PROS disorder is Klippel-Trenaunay syndrome. As used herein, the term "Klippel-Trénaunay syndrome" refers to a rare congenital medical condition in which blood vessels and/or lymph vessels fail to form properly.

Thus, the method according to the present invention can be supplied to a subject, who has been diagnosed as presenting one of the disorders in PROS.

As used herein, the term "subject" refers to any mammals, such as a rodent, a feline, a canine, and a primate. Particularly, in the present invention, the subject is a human afflicted with or susceptible to be afflicted with PROS disorders. In a particular embodiment, the subject is a human afflicted or susceptible to be afflicted with CLOVES syndrome. In a particular embodiment, the subject is a human afflicted or susceptible to be afflicted with Klippel-Trénaunay syndrome.

As used herein, the term "BYL719" is an ATP-competitive oral PI3K inhibitor selective for the p110α isoform that is activated by a mutant PIK3CA gene (Furet P., et al. 2013; Fritsch C., et al 2014). This molecule is also called Alpelisib and has the following formula in the art:

A "therapeutically effective amount" is intended for a minimal amount of active agent which is necessary to impart therapeutic benefit to a subject. For example, a "therapeutically effective amount" to a subject is such an amount which induces, ameliorates or otherwise causes an improvement in the pathological symptoms, disease progression or physiological conditions associated with or resistance to succumbing to a disorder. It will be understood that the total daily usage of the compounds of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 1,000 mg per adult per day. Typically, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

The PIK3CA inhibitor as described above may be combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The polypeptide (or nucleic acid encoding thereof) can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active polypeptides in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The invention will be further illustrated by the following figures and examples. However, these examples and figures should not be interpreted in any way as limiting the scope of the present invention.

FIGURES

FIGS. 1A-1C: Characterization of the mouse model of PROS and efficacy of the BYL719.

FIGS. 2A-2B: Efficiency of the BYL719 in an adult patient with severe CLOVES syndrome.

EXAMPLE

Material & Methods Animals

For this study, we interbedded homozygous R26Stop$^{FL}$P110* (Stock #012343) and heterozygous CAGGCre-ER™ (Stock #004682) on C57BL/6 background obtained from The Jackson Laboratories. We obtained R26Stop$^{FL}$P110*$^{+/-}$×CAGGCre-ER™+(referred here as PIK3CA$^{CAGG\text{-}CreER}$) and R26Stop$^{FL}$P110*$^{+/+}$×CAGGCre-ER™ (referred here as PIK3CA$^{WT}$). Animals were fed ad libitum and housed at constant ambient temperature in a 12-hour light cycle. Animal procedures were approved by the Departmental Director of "Services Vétérinaires de la Préfecture de Police de Paris" and by the ethical committee of the Paris Descartes University. A single dose of tamoxifen (40 mg×kg$^{-1}$) was administered through oral gavage at the age of 21 days. For survival studies, mice were followed daily after tamoxifen gavage (PIK3CA$^{WT}$ n=16 and PIK3CA$^{CAGG\text{-}CreER}$ n=16). For therapeutic studies, mice were treated with the PI3KCA inhibitor BYL719 (Chem Express; 50 mg×kg$^{-1}$ in 0.5% carboxymethylcellulose (Sigma), daily p.o.) or vehicle (0.5% carboxymethylcellulose (Sigma), daily p.o.). Treatment was started in the meantime of tamoxifen gavage for the preventive study (PIK3CA$^{CAGG\text{-}CreER}$ n=18) or ten days after for the therapeutic study (PIK3CA$^{CAGG\text{-}CreER}$ n=6). A total of 6 mice were sacrificed on day 51 after tamoxifen gavage in the vehicle group of the PIK3CA$^{CAGG\text{-}CreER}$, 6 mice on day 51 after tamoxifen gavage in the preventive BYL719 group and 6 mice on day 70 after tamoxifen gavage in the therapeutic study of the PIK3CA$^{CAGG\text{-}CreER}$ for tissues examination.

Cell Cultures

Breast cancer cell lines T-47D were obtained from Sigma Aldrich. Cells were cultured in media with DMEM+2 mM Glutamine+10% Fetal Bovine Serum (FBS). For BYL719 experiments (Chem Express), cells were treated with increasing concentration of BYL719 (0, 0.5, 1 and 5 µmol/L) for 2, 4 and 6 hours before western blot was performed. Each experiment was performed in duplicate and repeated at least three times.

Morphological Analysis

Mousse tissues were fixed in 4% paraformaldehyde, paraffin embedded. 4-µm sections of liver were stained with periodic acid Schiff (PAS), 4-µm sections of liver of spleen were stained with hematoxylin and eosin (H&E) and 4-µm sections of kidneys were stained with Masson's trichrome.

Immunohistochemistry and Immunofluorescence

4-µm sections of paraffin-embedded kidneys were incubated with anti-P-AKT (Ser$^{473}$) antibody (Cell Signaling Technology, ref #4060), anti-P-S6RP antibody (Cell Signaling Technology, ref #5364) and anti-CD34 antibody (eBioscience, ref #14-0341). Immunofluorescence studies were analyzed using the confocal microscope Zeiss LSM 700.

Western Blot

Western blots were performed as previously described[21]. Briefly, protein extracts from liver, muscles, heart, kidneys and T-47D cells were resolved by SDS-PAGE before being transferred onto the appropriate membrane and incubated with anti-P-AKT (Ser$^{473}$) antibody (Cell Signaling Technology, ref #4060), anti-P-AKT (Thr$^{308}$) antibody (Cell Signaling Technology, ref #13038), anti-P-S6RP antibody (Cell Signaling Technology, ref #5364), anti-GAPDH (Merck Millipore, ref #374) and anti-β actin antibody (Sigma-Aldrich, ref #A2228), followed by the appropriate peroxidase-conjugated secondary antibody. Chemiluminescence was acquired using a Fusion FX7 camera (Vilbert Lourmat) and densitometry was performed using Bio1D software (Certain Tech).

Patients

This study was performed in the Renal Division of Necker Hospital, starting in September 2015. The patient with the CLOVES syndrome had clinical examination, tumor measurements, naevi measurement before treatment instauration. BYL719 treatment was initiated at the dose of 250 mg orally per day. The study was conducted on two patients, an adult and a child, followed at Necker hospital. This protocol was approved by the ANSM (authorization no 553984-986 and no 584018); informed written consent was obtained from each patient or their legal representative. BYL719 was compassionately offered by Novartis. The first patient received 250 mg/day and the second patient 50 mg/day. BYL719 was orally delivered every morning before breakfast. Glycaemia was monitored after any meal during two months and then progressively sparse.

Data Analysis and Statistics

Data were expressed as means±SEM. Survival curves were analyzed with a Mantel-Cox (log-rank) test. Differences between the experimental groups were evaluated using ANOVA, followed when significant (P<0.05) by the Tukey-Kramer test. When only two groups were compared, Mann-Whitney tests were used. The statistical analysis was performed using Graph Prism Software.

Renal Function

The serum creatinine level was measured weekly during the first year and every 3 months thereafter using a Synchron Cx4 autoanalyzer (Beckman Coulter, Villepinte, France). The glomerular filtration rate was estimated using the MDRD formula (eGFR).

Biopsy Samples and Morphological Analysis

Kidney biopsy specimens were fixed in alcohol-formalin-acetic acid solution and embedded in paraffin. Four-micrometer sections were stained with the Periodic Acid Schiff (PAS) stain, Masson's trichrome and hematoxylin and eosin (H&E). Electron microscopy analyses were performed.

Immunohistochemistry and Immunofluorescence

Four sections of paraffin-embedded kidneys were incubated with anti-nephrin antibody (Progen), anti-WT1 antibody (Dako), anti-podocin antibody (Sigma) and anti-synaptopodin antibody (Novus Biologicals). Upon the total glomerular area. For each biopsies, all glomerular section were quantified. The primary antibodies were revealed with the appropriate Alexa 488- or 555-conjugated secondary antibodies (Molecular Probes). Immunofluorescence staining was visualized using the Zeiss LSM 700 confocal microscope. The podocyte-stained area was automatically quantified using a Nikon digital camera Dx/m/1200 and Image J software and expressed as the percentage of the podocyte-stained area.

In Situ Hybridization

Alcohol-formalin-acetic acid solution-fixed, paraffin-embedded tissues were assayed for PI3KCα RNA expression using a previously described digoxygenin-anti-digoxygenin technique. Nitroblue tetrazolium-5-bromo-4-chloro-3-indolyl phosphate toluidinium (NBT-BCIP) was used to visualize infected cells in the tissues. The specificity of the hybridization signal was systematically checked by hybridizing sense probes with parallel sections and anti-sense probes with uninfected renal tissues. ISH-stained tissues were visualized and photographed with an Olympus Proxis microscope and a Zeiss Axio Cam ICc1.

Cell Culture

Human fibroblasts were grown in DMEM supplemented with 15% FBS, penicillin (50 IU/ml)/streptomycin (50 µg/ml), and nonessential amino acids (Invitrogen).

Western Blot

Western blot were performed as previously described, using a rabbit antibody to human phospho-p70 S6 kinase (Thr389) (Cell Signaling Technologies) at 1:1000 followed by a horseradish peroxidase-conjugated antirabbit secondary antibody at 1:10,000 (Dako). The phosphorylation status of the p70 S6 kinase at the Thr389 site is specific for mTOR phosphorylation. A mouse monoclonal anti-b-actin antibody (Sigma-Aldrich, Lyon, France) was used as control. Protein phosphorylation levels were normalized to the matching densitometric values of b-actin.

DNA Sequencing

DNA was extracted using standard techniques from peripheral blood mononuclear cells (PBMCs) taken from the patient and skin biopsy in the tumor area. Mutation screening was performed by direct sequencing of all the PI3KCα exons and flanking intronic regions.

Volumetric Determination

Magnetic resonance imaging (MRI) was used to determine the volume of each tumor. MRI was performed at day 0 before BYL719 initiation and then monthly. In brief, the volume was calculated by summing the products of the area measurements and slice thickness.

Data Analysis and Statistics

The data were expressed as the means±SD. Differences among the experimental groups were evaluated using ANOVA, followed when significant by the Tukey-Kramer test. When only two groups were compared, the Mann-Whitney test was used. Probability values <0.05 were considered statistically significant. Analyses were performed with GraphPad Prism 5 (GraphPad software, La Jolla, CA).

Results

Inventors have observed a significant reduction of the size of the overgrown tissues in the subject, which was administered with BYL719. After a month of treatment, the patient weight decreased from 83.5 kg to 73.5 kg. This weigh loss was related to a dramatic reduction of the oedema and an improvement of the global cardiac function rate (cardiac output was 22 l/min in December 2015 before treatment and measured at 8l/min on February the 8th). The plasmatic brain natriuretic peptide levels decreased from 2500 pg/ml to 240 pg/ml at day 30 confirming the improvement of the heart failure. The subcutaneous tumour sizes showed a global reduction of 10 percent after 30 days of treatment as assed by the CT scan and Magnetic Resonance Imaging (MRI). The Karnofsky performance status scale of the patient improved from 40 to 60% in 30 days. Haemoglobin level increased from 8 g/dl to 11.8 g/dl.

Some skin areas (left ear) showed accelerated age phenotype before treatment that were improved after a month of BYL719 administration. Furthermore, several large naevi showed decolouration after the beginning of the treatment.

A Mouse Model of PROS

Figure 1A:
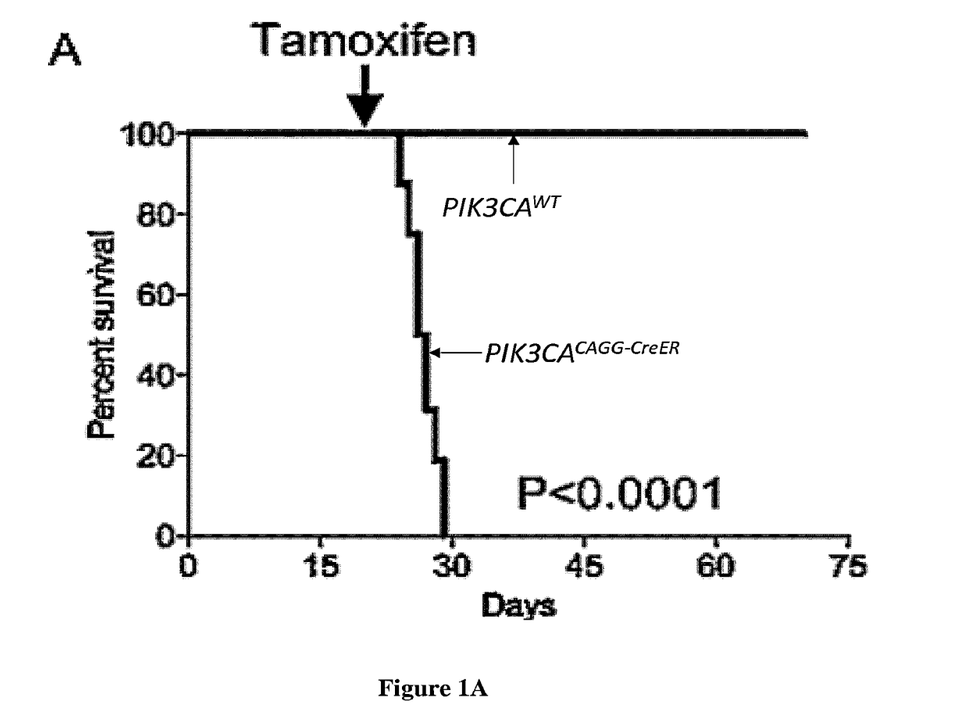
FIG. 1A) Kaplan-Meier survival curves of PIK3CA$^{WT}$ and PIK3CA$^{CAGG\text{-}CreER}$ mice after tamoxifen administration.
Figure 1B:
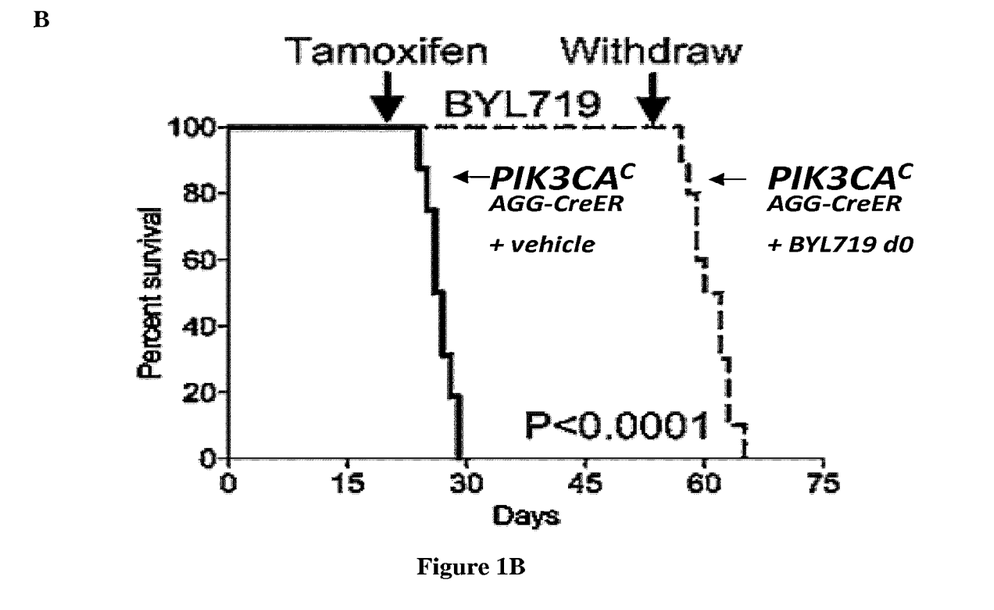
FIG. 1B) Kaplan-Meier survival curves of P/K3CA$^{CAGG\text{-}CreER}$ mice treated or not with BYL719 after tamoxifen administration. After 40 days of treatment the BYL719 is withdrawn.

We began this study by developing a mouse model of PROS. To this end, we took advantage of the transgenic mouse strain R26StopFLP110*. These mice allow for inducible expression of activated PI3KCA heterodimer in a tissue-specific manner. R26StopFLP110* mice were crossed with CAGG-CreER mice to generate PIK3CA$^{CAGG\text{-}CreER}$ animals that ubiquitously overexpress PIK3CA upon tamoxifen administration. Three weeks old mice were treated with a single dose of 40 mg·kg$^{-1}$ tamoxifen to induce Cre recombination[16]. We observed that compared to the control PIK3CA$^{WT}$ mice, the PIK3CA$^{CAGG\text{-}CreER}$ mice started to die on day 3 post Cre induction with an average of 6 days post Cre recombination (FIG. 1A). Death occurring suddenly in most cases, with necropsy revealing intraabdominal and hepatic hemorrhages (data not shown). Some mice displayed difficulty walking with hypertrophic psoas muscle assessed by the magnetic resonance imaging (MRI) (data not shown). Additionally, whole body MRI showed the rapid occurrence of scoliosis, vessels abnormalities, kidney cysts, and muscles hypertrophy. Histological examination revealed multiple organs abnormalities including severe liver steatosis with vessel disorganization (data not shown), loss of integrity of the spleen microarchitecture (data not shown), spontaneous hemorrhage, and fibrosis of the kidney with aberrant vessels. To further characterize the vessels abnormalities, we performed CD34 immunostaining that confirmed the presence of severe vessel dilation. As expected, western blot and immunofluorescence studies showed AKT/mTORC pathway activation in all examined organs. We therefore concluded that the PIK3CA$^{CAGG\text{-}CreER}$ mice recapitulate human PROS phenotype.

BYL719 Prevents and is an Effective Therapy for PROS in Mice

Figure 1C:
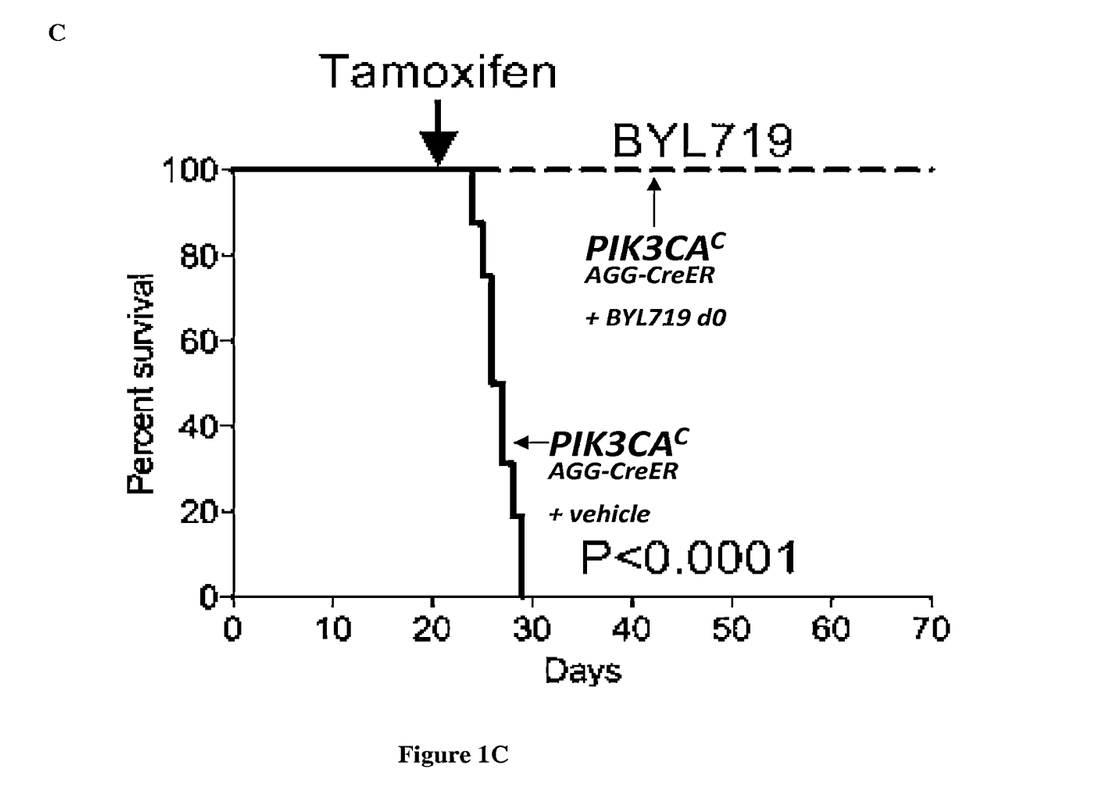
FIG. 1C) Kaplan-Meier survival curves of PIK3CA$^{CAGG\text{-}CreER}$ mice treated or not with BYL719 10 days after tamoxifen administration. Scale bars 10 µm.

We decided to test the impact of BYL719 in PIK3CA$^{CAGG\text{-}CreER}$ mice. To this aim, we first performed a preventive study where the BYL719 was orally administrated starting just after Cre induction (data not shown). We observed that daily administration of BYL719 dramatically improved animal survival (FIG. 1C). In fact, while all PIK3CA$^{CAGG\text{-}CreER}$ mice in the placebo group died within 21 days, PIK3CA$^{CAGG\text{-}CreER}$ mice treated with BYL719 were alive 40 days later with overtly normal appearance. Importantly, treatment interruption 40 days after Cre recombination lead to the death of all the PIK3CA$^{CAGG\text{-}CreER}$ animals. We sacrificed several PIK3CA$^{CAGG\text{-}CreER}$ mice receiving BYL719 on day 40 after Cre induction. Histological examination showed that mice treated with BYL719 had preserved tissues (data not shown) and normal vessels (data not shown). Western blot and immunofluorescence confirmed the efficiency of BYL719 at inhibiting PI3KCA activation (data not shown).

Next, we performed a therapeutic study by giving either the placebo or the BYL719 to PIK3CA$^{CAGG\text{-}CreER}$ mice ten days after Cre induction, when mice begin to die (FIG. 1C). On day 10 after Cre induction, MRI confirmed the presence of tissue abnormalities as described previously (data not shown). While the placebo group mice died within the next following days, BYL719 dramatically improved the survival of PIK3CA$^{CAGG\text{-}CreER}$ mice. MRI performed 12 days after the beginning of the treatment (22 days after Cre induction) demonstrated very rapid improvement of scoliosis, muscle hypertrophy, and vessel abnormalities (data not shown). Histological analysis revealed that BYL719 treated mice displayed no, or only minor, tissue changes (data not shown). As in the preventive study, western blot and immunofluorescence confirmed PIK3CA inhibition (data not shown).

We concluded that the BYL719 was able to dramatically improve PROS mice, suggesting it may be an effective therapeutic option for PROS patients for whom no medication currently exists.

Effect of BYL719 in Human Cells with PIK3CA Mutation

Next, we examined the efficacy of BYL719 at inhibiting the PIK3CA pathway in human cells. To this aim, we used T-47D human cells derived from breast cancer. These cells harbor heterozygous mutation of the PIK3CA c.3140A>G (H1047R). This gain of function mutation is also the most frequent mutation observed in PROS patients[6].

We first confirmed in these cells, the spontaneous activation of the AKT/mTORC pathway as assessed by the phosphorylation status of AKT on the residue Thr$^{308}$ and Ser$^{473}$ but also the phosphorylation of the S6RP protein (data not shown). Then, cells were exposed to increasing concentrations of BYL719. We observed that, after 2 hours of BYL exposure at a concentration of 1 μmol/L, the AKT/mTORC pathway was fully inhibited (data not shown). The effect was similar when the cells were exposed to 4 and 6 hours to BYL719.

These data suggested that BYL719 is able to inhibit the PI3KCA activation in human cells with PIK3CA c.3140A>G (H1047R) mutation.

Dramatic Impact of BYL719 in Patients with PROS

Based on these results, we decided to administer BYL719 as a compassionate use for two patients, one adult and one child, who suffered from extremely severe clinical manifestation of CLOVES syndrome and were experiencing therapeutic failure and life threatening complications. Patient 1 was a 29 years old man with mosaicism and biopsy proven gain of function mutation PIK3CA c.3140A>G (H1047R). He had overgrowth syndrome characterized by left leg hypertrophy, scoliosis, multiple naevi and extremely severe vascular abnormalities (data not shown). He underwent multiple aggressive debulking surgeries to remove abdominal and dorsal vascular tumors, as well as multiple angiographies with embolization to limit tumor growth. He became paraplegic at the age of 20 years old due to spinal cord compression and required bladder stenting to drain his urine. He developed progressively worsening severe systolic heart failure with a measured cardiac output of 18 l/min and a Brain Natriuretic Peptide (BNP) level constantly over 2500 pg/mL (N<100 pg/mL), resistant to all usual drugs. It is unclear whether the heart failure was due to the presence of vascular shunts, PIK3CA mutation in the cardiac cells, or both. During 5 years, the patient received rapamycin to limit tumor growth progression but without any efficiency. Lastly, the patient developed kidney dysfunction with severe proteinuria. Kidney biopsy revealed glomerular lesions with extensive fibrosis. Kidney lesions may be the result of heart dysfunction, the use of rapamycin[11], and/or PIK3CA mutation in kidney epithelial cells. CT scan (data not shown) and MRI (data not shown) showed severe vascular abnormalities, while PET-scan was negative. Due to the severity of the case with poor prognosis, physicians, surgeons and radiologists decided to stop any interventional treatment and to provide him only supportive and palliative care. His vital prognosis was engaged with survival estimated at few months.

Figure 2A:
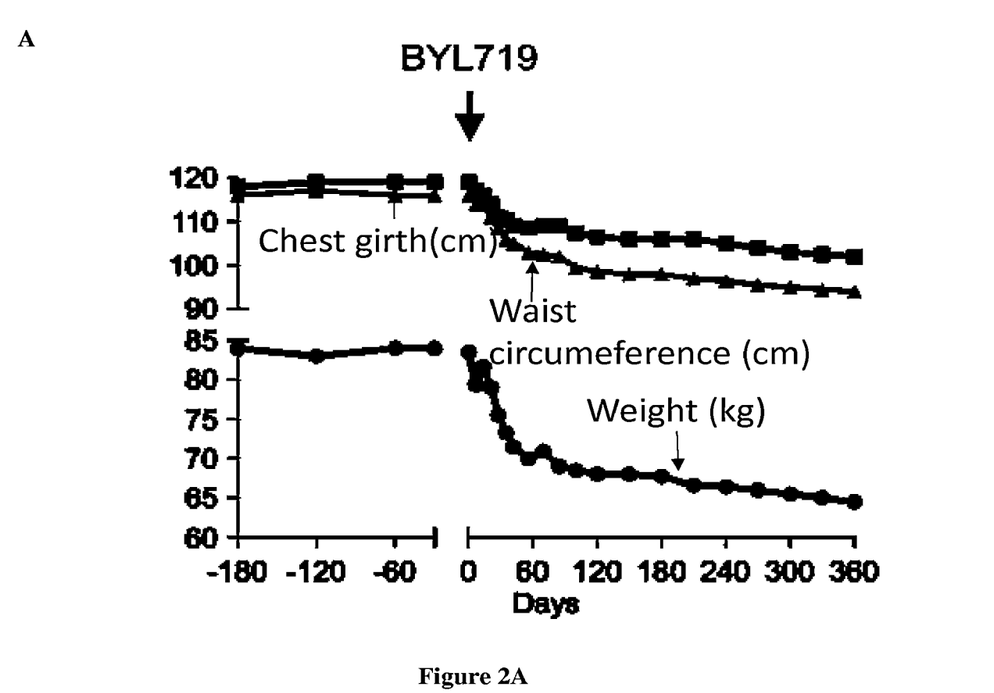
FIG. 2A) Clinical parameters (weight, chest girth and waist circumferences) of the patient 1 before and after BYL719 initiation.
Figure 2B:
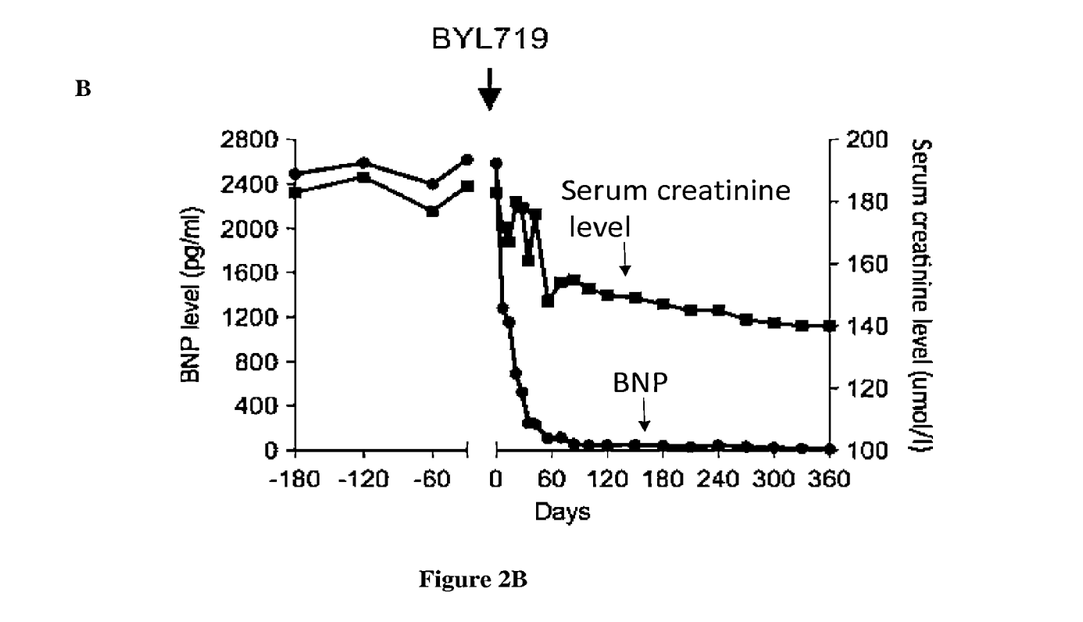
FIG. 2B) Brain Natriuretic Peptide (BNP) and serum creatinine levels before and after BYL719 initiation.

Following our experimental findings and after ethical consideration we decided to purpose the BYL719 to our patient. We obtained the approbation from Novartis and the French regulatory agency (Agence nationale de sécurité du medicament et des produits de santé, ANSM) to deliver the BYL719 as a compassionate use. We stopped rapamycin and one month later we started the BYL719. The drug was orally delivered every day. We choose 250 mg per day as a starting dosage, the lowest dose used in clinical trial and based on our in vitro data. Within the first few days we observed a dramatic improvement of the general status of the patient. The patient started to feel better and more comfortable. Week after week we could objective a dramatic effect of the drug on tumors sizes, venous dilation and skin aspect (data not shown). He lost 23 kg in 12 months due to edema clearance but also due to a major reduction of all vascular tumor abnormalities (data not shown). The circumference of the thorax and the abdomen reduced dramatically, Δ-20% and Δ-35% in 12 months respectively (FIG. 2A). CT-scan and MRI confirmed global vascular tumors shrinkage with a 63% volume decreased at 12 months, as well as subcutaneous infiltration disappearance (data not shown). The effect of the drug on the heart function was remarkable, with a complete correction of the BNP level in the course of 4 weeks (FIG. 2B). The cardiac output dropped to 3 l/min, and the size of the heart reduced of 25% as determined by CT scan (data not shown). Left ventricular mass indexed to body surface area decreased from 250 g/m$^2$ to 148 g/m$^2$. Renal function was also rapidly improved with an estimated glomerular filtration rate increasing from 33 to 52 ml/min/1.75 m$^2$ (FIG. 3D). The volume of the hypertrophic left leg also reduced (data not shown). We observed a dramatic improvement of the skin hypertrophy with a change in the nevus coloration and a reduction of the size of the ear (data not shown). Lastly, 6 months after BYL719 initiation the patient began to have partial gain bladder function with improvement of saddle anesthesia. MRI revealed a 60% reduction in size of the venous malformation that was compressing the spinal cord. Twelve month later, the patient had no side effect except hyperglycemia that was well controlled by regimen. The patient is still receiving the BYL719.

Figure 3:
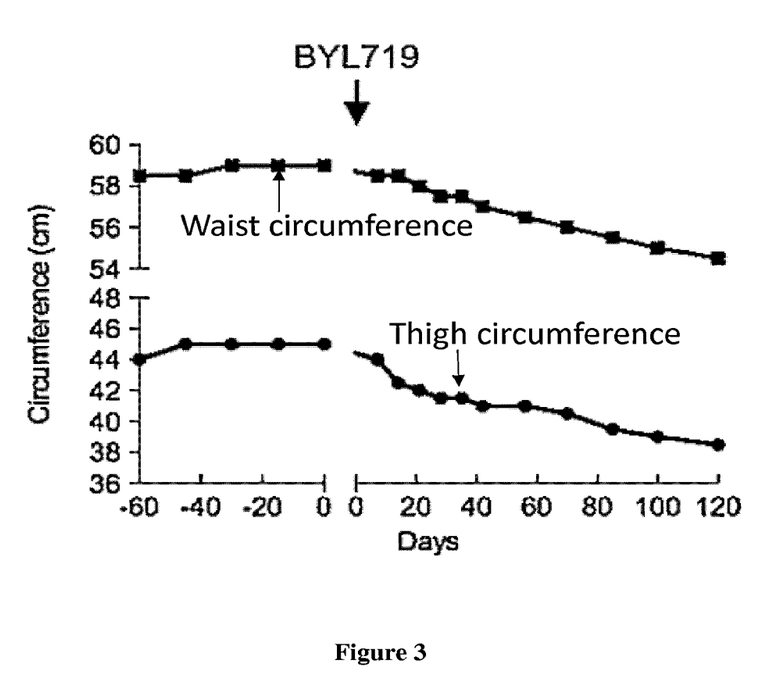
FIG. 3: Efficiency of the BYL719 in a child patient with severe CLOVES syndrome. Clinical parameters (thigh and waist circumferences) of the patient 2 before and after BYL719 initiation.

Patient 2 was a 9 years old girl with a CLOVES syndrome diagnosed two years prior to this study and biopsy verified gain of function mosaicism mutation in PIK3CA c.3140A>G (H1047R). She had scoliosis, left leg hypertrophy, vascular abnormalities and hypertrophic muscle of the back (data not shown). Importantly, she had a voluminous cystic lymphangioma involving the left kidney and the gastrointestinal tract. PET-scan showed metabolic fixation of the thymus, muscle from the back and the left leg (data not shown). The intraabdominal tumor was growing rapidly, with surgical or interventional radiology deemed impossible. After ethical consideration, we obtained the approbation from Novartis and the French regulatory agency (ANSM) to provide BYL719. Since the drug has never been tested in a child, we decided to start at the lowest available dosage, 50 mg/day. As with the first patient, we observed a dramatic clinical improvement rapidly after the beginning treatment (data not shown). The patient reported improved comfort and we observed a 15% reduction in the volume of the left leg, the left foot (1 shoe size reduction), and 8% of her abdominal circumference (data not shown) in 120 days. Hypertrophic muscles of the back shrunk rapidly and, unexpectedly, her scoliosis was reversed in 120 days without any other intervention (FIG. 3). More importantly, MRI showed a 60% reduction of the volume of the intraabdominal tumor in only 4 months. PET-scan performed 4 months after treatment initiation confirmed the reduction of the disease in almost all tissues. During the follow up, we found the normal growth of this patient was not impacted by the BYL719, and she reported no side effects. The patient is still receiving treatment.

Discussion

Here, we report the first mouse model of PROS that recapitulates the human phenotype, a rescue of PROS in the mouse model by treatment with the PI3CA inhibitor BYL719, and, using a translational approach, have demonstrated the efficacy of BYL719 in PROS patients. This study provides the first direct evidence supporting PIK3CA inhibition as a robust and effective therapeutic strategy in the previously untreatable PROS.

BYL719 treatment promoted the recovery of two patients, an adult and a child, with positive clinical impact observable rapidly after initiation of treatment. As in the mouse model, the drug improved all organ dysfunctions related to PROS. Importantly, the drug maintained efficacy in improving malformations during the entire treatment period. The drug was well tolerated, without any significant side effects, in contrast to mTOR inhibitors. As anticipated, given that PI3KCA is downstream of the insulin receptor, hyperglycemia occurred in the first patient, indicating that caution should be exercised given the potential for long-term side effects, particularly in children where growth, fertility, and puberty could be affected. However, during the treatment period the growth of the child was not affected, and any detrimental effects must be weighed against the benefits in this devastating and previously intractable disease. Several questions remain, including when the best period is to start the treatment and when or if it therapy can be halted. Given the mouse data it seems highly possible that withdraw of the drug would be associated with the restart of the diseases, as is also seen in patients with Tuberous Sclerosis[17].

PIK3CA is one of the most commonly mutated oncogenes in human cancers, and similar mutations are found in PROS patients[6]. As in cancer, although PIK3CA mutations can be detected across the entire coding sequence of the gene, most of the mutations are found in 3 major hotspot clusters in the helical (E542K, E545K) and kinase domains (H1047R). Each of these mutations leads to gain-of-function activation of PIK3CA pathway. Importantly, in cancer models, BYL719 is able to fully block the activity of the pathway regardless of the type of mutation[14]. Additionally, our mouse model of PROS based on an increased number of copy of the PIK3CA gene, is rescued by the BYL719. Taking together these data suggest that the drug is certainly efficient in all form of PROS and not only acting on the H1047R mutation.

This discovery may have broad clinical impact. Importantly, if PROS are rare, they are not exceptional. The number of PROS patients is assumed to be largely underestimated due to phenotype heterogeneity leading to misdiagnosis. Mosaicism often requires the use highly sensitive technologies to detect PIK3CA somatic alteration[6]. With an incidence of 1/100,000 the recent proposal to include patients with Klippel-Trenaunay syndrome into the PROS highlights the great number of patients that may benefit from BYL719[9]. Importantly, PROS is an evolving entity since more and more diseases, such as isolated venous malformations can also be linked to PIK3CA mutations[8,18,19].

Our mouse model offers a unique opportunity to better understand the physiopathology of the PROS. This model recapitulates PROS with vasculature abnormalities, muscle hypertrophy, kidney dysfunction, liver steatosis, spleen disorganization and scoliosis. Severity was related to the high percentage of Cre recombination events induced by tamoxifen treatment. The mice perished due to severe bleeding, particularly from the mesenteric and liver vessels. Bleeding and leakage are among the severe complication observed in patients with CLOVES syndrome[6]. We also found that overexpression of the PIK3CA gene in the liver lead to steatosis as in the genetic overactivation of the AKT/mTORC[20]. Remarkably, the mice quickly developed scoliosis after Cre recombination. This lesion is certainly due to the development of hypertrophic paraspinal-truncal soft tissue masses, since the BYL719 was able to quickly reverse the abnormalities. The improvement of scoliosis was also visible in the two patients with reduction in muscle masses and hypermetabolic signal. BYL719 was able to either prevent the development of any tissue abnormalities or to rescue all defects while disease was achieved.

In conclusion, the results of this work indicate that PIK3CA inhibition may be a safe and effective means to improve health and quality of life in PROS patients. Obviously, these results will have to be confirmed in larger cohort of patients but, they represent the most promising available therapy for patient with PROS.

Throughout this application, various references describe the state of the art to which this invention pertains. The disclosures of these references are hereby incorporated by reference into the present disclosure.

The invention claimed is:

1. A method of treating a patient who is an adult having a PIK3CA-related overgrowth spectrum (PROS) disorder, comprising the steps of
   identifying the subject as suffering from the PROS disorder having an overgrowth of multiple organs or tissues caused by a somatic mosaic mutation, wherein the PROS disorder is not an isolated venous malformation;
   administering orally to the subject a therapeutically effective amount of BYL719, wherein the therapeutically effective amount of BYL719 is a starting dose of 250 mg daily; and
   reversing the overgrowth of multiple organs or tissues.

2. The method of claim 1, wherein the somatic mosaic mutation is a mutation in the PIK3CA gene selected from the group consisting of H1047R, E542K and E545K.

3. The method of claim 1, wherein the PROS disorder is not responsive to treatment with rapamycin.

4. The method of claim 1, wherein the PROS disorder is selected from the group consisting of
   fibroadipose overgrowth;
   megalencephaly-capillary malformation syndrome;
   congenital lipomatous overgrowth, vascular malformations, epidermal nevi, skeletal and spinal anomalies and/or scoliosis (CLOVES) syndrome;
   hemihyperplasia multiple lipomatosis; and
   Klippel-Trenaunay syndrome.

5. The method of claim 4, wherein the PROS disorder is congenital lipomatous overgrowth, vascular malformations, epidermal nevi, skeletal and spinal anomalies, and/or scoliosis (CLOVES) syndrome.

6. The method of claim 4, wherein the PROS disorder is Klippel-Trenaunay syndrome.

7. The method of claim 1, wherein the method treats a symptom selected from the group consisting of edema, venous dilation, vascular tumors, elevated brain natriuretic peptide blood level, proteinuria, kidney dysfunction, overgrown tissue, dysregulated adipose tissue, scoliosis, enlarged bony structures without progressive bony overgrowth, benign tumors, megalencephaly-capillary malformation, lipomatous asymmetric overgrowth of the trunk, epidermal nevi, lymphatic malformation, muscle hypertrophy, liver steatosis, and spleen disorganization.

8. A method of treating a patient who is a child having a PIK3CA-related overgrowth spectrum (PROS) disorder, comprising the steps of
   identifying the subject as suffering from the PROS disorder having an overgrowth of multiple organs or tissues caused by a somatic mosaic mutation, wherein the PROS disorder is not an isolated venous malformation;
   administering orally to the subject a therapeutically effective amount of BYL719, wherein the therapeutically effective amount of BYL719 is a starting dose of 50 mg daily; and
   reversing the overgrowth of multiple organs or tissues.

9. The method of claim 8, wherein the somatic mosaic mutation is a mutation in the PIK3CA gene selected from the group consisting of H1047R, E542K and E545K.

10. The method of claim 8, wherein the PROS disorder is not responsive to treatment with rapamycin.

11. The method of claim 8, wherein the PROS disorder is selected from the group consisting of
   fibroadipose overgrowth;
   megalencephaly-capillary malformation syndrome;

congenital lipomatous overgrowth, vascular malformations, epidermal nevi, skeletal and spinal anomalies and/or scoliosis (CLOVES) syndrome;
hemihyperplasia multiple lipomatosis; and
Klippel-Trenaunay syndrome.

12. The method of claim 11, wherein the PROS disorder is congenital lipomatous overgrowth, vascular malformations, epidermal nevi, skeletal and spinal anomalies, and/or scoliosis (CLOVES) syndrome.

13. The method of claim 11, wherein the PROS disorder is Klippel-Trenaunay syndrome.

14. The method of claim 8, wherein the method treats a symptom selected from the group consisting of edema, venous dilation, vascular tumors, elevated brain natriuretic peptide blood level, proteinuria, kidney dysfunction, overgrown tissue, dysregulated adipose tissue, scoliosis, enlarged bony structures without progressive bony overgrowth, benign tumors, megalencephaly-capillary malformation, lipomatous asymmetric overgrowth of the trunk, epidermal nevi, lymphatic malformation, muscle hypertrophy, liver steatosis, and spleen disorganization.

\* \* \* \* \*